United States Patent
Coste

(10) Patent No.: US 11,026,878 B2
(45) Date of Patent: Jun. 8, 2021

(54) MAKEUP-FIXING COSMETIC COMPOSITION

(71) Applicant: LABORATOIRE GARANCIA, Paris (FR)

(72) Inventor: Savéria Coste, Paris (FR)

(73) Assignee: LABORATOIRE GARANCIA, Paris (FR)

( * ) Notice: Subject to any disclaimer, the term of this patent is extended or adjusted under 35 U.S.C. 154(b) by 163 days.

(21) Appl. No.: 16/335,316

(22) PCT Filed: Sep. 25, 2017

(86) PCT No.: PCT/FR2017/000177
§ 371 (c)(1),
(2) Date: Mar. 21, 2019

(87) PCT Pub. No.: WO2018/055244
PCT Pub. Date: Mar. 29, 2018

(65) Prior Publication Data
US 2020/0016060 A1   Jan. 16, 2020

(30) Foreign Application Priority Data
Sep. 25, 2016   (FR) ...................................... 1670549

(51) Int. Cl.
| | | |
|---|---|---|
| *A61K 8/73* | (2006.01) | |
| *A61Q 1/00* | (2006.01) | |
| *A61K 8/9794* | (2017.01) | |
| *A61K 8/9789* | (2017.01) | |
| *A61K 8/81* | (2006.01) | |

(52) U.S. Cl.
CPC .............. *A61K 8/73* (2013.01); *A61K 8/8117* (2013.01); *A61K 8/8152* (2013.01); *A61K 8/9789* (2017.08); *A61K 8/9794* (2017.08); *A61Q 1/00* (2013.01)

(58) Field of Classification Search
CPC ...... A61K 8/73; A61K 8/8117; A61K 8/8152; A61K 8/9789; A61K 8/9794; A61Q 19/08; A61Q 1/00; A61Q 1/02; A61Q 1/08; A61Q 1/10
See application file for complete search history.

(56) References Cited

U.S. PATENT DOCUMENTS

| | | | | |
|---|---|---|---|---|
| 2007/0166257 A1* | 7/2007 | Atis | ....................... | A61Q 19/00 424/70.7 |
| 2009/0028969 A1* | 1/2009 | Sene | ...................... | A61K 8/602 424/757 |

FOREIGN PATENT DOCUMENTS

| | | |
|---|---|---|
| EP | 1018334 A1 | 7/2000 |
| FR | 2837388 A1 | 9/2003 |
| FR | 2856925 A1 | 1/2005 |
| WO | WO-2015188335 A1 * 12/2015 | ............... A61K 8/26 |

OTHER PUBLICATIONS

International Search Report and Written Opinion in corresponding International Patent Application No. PCT/FR2017/000177 dated Dec. 11, 2017. 19 pages.
International Preliminary Report on Patentability in corresponding International Patent Application No. PCT/FR2017/000177 dated Mar. 26, 2019. 7 pages.
No Author. "Cushion Massage Blusher." Mintel. www.gnpd.com. Aug. 31, 2016. XP002765089. 4 pages.
No Author. "Crunchy Cereal with Milk Chocolate." Mintel. www.gnpd.com Feb. 29, 2016. XP002765088. 4 pages.

\* cited by examiner

*Primary Examiner* — Ernst V Arnold
(74) *Attorney, Agent, or Firm* — Leason Ellis LLP

(57) ABSTRACT

The present invention proposes a new way of having makeup last longer on the skin. The present invention comprises the supply and use of a new liquid cosmetic composition comprising the combining of styrene/acrylates copolymer and Biosaccharide Gum-4 preferably in an aqueous solution. This makeup-fixing composition is intended to be sprayed on top of makeup compositions, after they have been applied to the skin, so as to delay the deterioration of makeup compositions and thus having the makeup last longer.

2 Claims, 3 Drawing Sheets

MAKEUP-FIXING COSMETIC COMPOSITION

CROSS-REFERENCE TO RELATED PATENT APPLICATIONS

This application is a U.S. National Stage Application under 35 U.S.C. § 371 of International Patent Application No. PCT/FR2017/000177, filed Sep. 25, 2017, which claims the benefit of priority under 35 U.S.C. Section 119(e) of French Patent Application number FR 1670549 filed Sep. 25, 2016, both of which are incorporated by reference in their entireties. The International Application was published on 29 Mar. 2018, as International Publication No. WO 2018/055244 A1.

PRIOR ART

For millennia, makeup has been used to improve the appearance of the face and to cover facial imperfections. Examples of said makeup compositions include, but are not limited to, foundation, powders, eye shadow, blusher, mascara and concealers.

Once applied to the skin, makeup generally deteriorates over the course of the day. The speed of the deterioration may be influenced by a number of factors, including, but not limited to, the characteristics of the ingredients, the user's skin type, the temperature of the skin, the temperature of the surroundings, the humidity of the surroundings, perspiration, etc.

Furthermore, the main makeup deterioration factor is rubbing, for example on clothes, handkerchiefs, or even upon contact with the skin; for example, for foundation, blusher and powder, when the user or a third party touches the user's face or when the user answers the telephone, for lipstick, upon kissing, or for eye shadow, due to the repeated opening and closing movement of the eyelids throughout the day.

This deterioration compromises the appearance of the makeup, and it is generally desirable for the makeup compositions to be resistant to deterioration of this kind.

For this purpose, a number of cosmetics manufacturers have created "long lasting" makeup products (for example foundations, mascaras, eye shadows, etc.). However, many users find these long-lasting products only partially satisfactory, given that (i) they are generally available only in a restricted number of galenics, colors and shades, (ii) they are generally difficult to remove, and (iii) they generally have a "non-natural" feel since the long-lasting products generally do not have the same "light" feel as standard makeup compositions.

Alternatively, the users may also use a makeup fixing spray in order to extend the duration of their cosmetic makeup products. These makeup fixing sprays are applied as a surface layer on the makeup composition, and act as a protective coating in order to help prevent the deterioration of the makeup compositions.

However, makeup fixing sprays of this kind tend to harden the makeup, which may cause discomfort for the user. Moreover, these makeup fixing sprays typically comprise polymers (for example acrylics) dissolved in a solvent, usually alcohol, which produces a layer of transparent lacquer on the makeup, which may appear artificial and cause some discomfort for the user.

In addition, some people find that the solvent (usually alcohol or glycol) used in these makeup fixing sprays may be an irritant for the skin. As a result, these sprays are used only as exceptions, and cannot be used every day, or even several times a day, by people whose skin and surroundings require it.

There is therefore a need for a new way of giving the makeup a more lasting hold, which is not affected by the above-mentioned drawbacks of the prior art.

THE INVENTION

The present invention proposes a new way of giving the makeup a more lasting hold on the skin, and which is not affected by the above-mentioned drawbacks of the prior art.

More particularly, the present invention comprises providing and using a new makeup fixing cosmetic composition that is intended to be applied on top of the makeup compositions after said compositions have been applied to the skin, so as to slow the deterioration of the makeup compositions and to thus extend the hold of the makeup.

A first object of the invention therefore relates to a makeup fixing cosmetic composition comprising the association of styrene/acrylates copolymer and Biosaccharide Gum-4 in an aqueous solution.

According to the present invention, "styrene/acrylates copolymer" is preferably intended to denote styrene/acrylate copolymer in the form of a film, and not in the form of particles.

According to the present invention, "Biosaccharide Gum-4" is intended to mean a branched anionic polysaccharide that is derived from sorbitol and comprises repeated units of L-fructose, 2-D-glucose and glucuronic acid, as described in the patent application FR2856925 and marketed under the designation Biosaccharide Gum-4. Adding said ingredient to the cosmetic compositions according to the invention makes it possible to prevent the appearance and/or reduce the imperfections and losses of luster in complexion, and wrinkles or lines associated with air pollution. In a surprising and unexpected manner, the applicant has demonstrated that the Biosaccharide Gum-4 considerably and synergistically increases the makeup fixing ability of the styrene/acrylates copolymer.

According to the invention, the makeup fixing cosmetic composition is preferably in liquid form and is intended to be sprayed onto the user's skin, on top of the makeup compositions. The makeup fixing cosmetic composition preferably comprises the association of styrene/acrylates copolymer and Biosaccharide Gum-4 in an aqueous solution. Preferably, again, the makeup fixing cosmetic composition comprises the association of styrene/acrylates copolymer and Biosaccharide Gum-4 in water.

According to the present invention, "water" is intended to mean distilled water. This is also intended to mean floral waters, preferably rose water, sage water, hamamelis water, and/or cornflower water.

"Rose water" is intended to mean rose petal water for cosmetic use; cleansing, balancing and calming, floral rose water is traditionally used for keeping the complexion clear. Said water also cleanses and balances sensitive skin, as a result of its astringent properties.

"Sage water" is intended to mean sage flower water for cosmetic use, which is used on account of its cleansing and antioxidant properties.

"Hamamelis water" is intended to mean hamamelis flower water for cosmetic use. Rich in tannins and flavonoids, hamamelis has astringent and anti-redness properties. Hamamelis tones and protects the small surface vessels of the epidermis which tend to weaken.

"Cornflower water" is intended to mean cornflower flower water for cosmetic use. Refreshing, decongesting and soothing, cornflower water is recommended in particular for soothing sensitive skin.

All the percentages mentioned in the present text refer to weight percentages of the composition.

According to the invention, the makeup fixing cosmetic composition according to the invention preferably comprises between approximately 0.25% and approximately 20% styrene/acrylates copolymer, and between approximately 0.012% and approximately 0.36% Biosaccharide Gum-4.

More preferably, according to the invention, the makeup fixing cosmetic composition according to the invention comprises between approximately 0.25% and approximately 20% styrene/acrylates copolymer, between approximately 0.012% and approximately 0.36% Biosaccharide Gum-4, between approximately 70% and approximately 99.738% water, and optionally cosmetically acceptable excipients.

Particularly preferably, according to the invention, the makeup fixing cosmetic composition according to the invention comprises between approximately 0.25% and approximately 2% styrene/acrylates copolymer, and between approximately 0.012% and approximately 0.09% Biosaccharide Gum-4.

More particularly preferably, according to the invention, the makeup fixing cosmetic composition according to the invention comprises between approximately 0.25% and approximately 2% styrene/acrylates copolymer, between approximately 0.012% and approximately 0.09% Biosaccharide Gum-4, between approximately 70% and approximately 99.738% water, and optionally cosmetically acceptable excipients.

Very particularly preferably, according to the invention, the makeup fixing cosmetic composition according to the invention comprises between approximately 0.25% and approximately 0.5% styrene/acrylates copolymer, and between approximately 0.06% and approximately 0.09% Biosaccharide Gum-4.

Most preferably, according to the invention, the makeup fixing cosmetic composition according to the invention comprises between approximately 0.25% and approximately 0.5% styrene/acrylates copolymer, between approximately 0.06% and approximately 0.09% Biosaccharide Gum-4, between approximately 70% and approximately 99.69% water, and optionally cosmetically acceptable excipients.

According to the invention, the makeup fixing cosmetic composition according to the invention may preferably additionally comprise one or more plant extracts.

Particularly preferably, according to the invention, the makeup fixing cosmetic composition according to the invention comprises an extract of a photoprotective plant. A "photoprotective plant" is intended to mean halophilic plants such as *Crithmum maritimum* or *Matricaria maritima*, or other plants such as *Urucum, Karanja, Polypodium leucotomos*, or *Buddleja officinalis*.

More particularly preferably, said photoprotective plant extract is the extract of *Buddleja officinalis* flowers. The extract of *Buddleja officinalis* flowers has a high concentration of phenylpropanoids, verbascoside and echinacoside, which gives it general photoprotective properties. Very particularly preferably, said *Buddleja officinalis* flower extract is titrated to at least 10%, preferably 15%, verbascoside, and at least 2%, preferably 3%, echinacoside.

More particularly preferably, the makeup fixing cosmetic composition according to the invention comprises between approximately 0.05% and approximately 0.5% of a *Buddleja officinalis* flower extract.

According to the invention, the makeup fixing cosmetic composition according to the invention preferably furthermore comprises between approximately 1% and approximately 10% *Oryza sativa* rice powder (rice starch).

According to the present invention, "rice powder" is intended to mean micronized rice for cosmetic use, having a grain size of less than 10 microns for example. Rich in vitamin B and E, iron, magnesium, phosphorous and starch, said rice powder has absorbent and mattifying properties, and is particularly suitable for sensitive skin because it has soothing qualities.

According to the invention, the makeup fixing cosmetic composition according to the invention advantageously additionally comprises one or more preservatives. Particularly preferably, according to the invention, the makeup fixing cosmetic composition according to the invention comprises between approximately 0.1% and approximately 3.5% preservative.

According to the present invention, "preservative" is intended to mean any preservative traditionally used in cosmetic compositions, for example parabens, phenoxyethanol, potassium sorbate, salicylic acid, sodium dehydroacetate, benzyl salicylate, benzyl alcohol, cetrimonium chloride, pentylene glycol, 12 hexanediol and chlorphenesin.

According to the invention, the makeup fixing cosmetic composition according to the invention advantageously additionally comprises one or more perfumes or perfumed compositions. Particularly preferably, according to the invention, the makeup fixing cosmetic composition according to the invention comprises between approximately 0.1% and approximately 3% perfume or perfumed composition.

According to the invention, the makeup fixing cosmetic composition according to the invention advantageously additionally comprises one or more organic solar filters (benzophenones, octocrylene, methylene bis-benzotriazolyl tetramethylbutylphenol, butyl methoxydibenzoylmethane, etc.), or titanium dioxide, or zinc oxide.

According to the invention, the makeup fixing cosmetic composition according to the invention preferably comprises
between 0.25% and 20% styrene/acrylates copolymer
between 0.012% and 0.36% Biosaccharide Gum-4
between 1% and 10% rice powder
between 0.05% and 0.5% *Buddleja officinalis* flower extract
between 1% and 30% rose water
between 1% and 30% cornflower water
between 1% and 30% hamamelis water
between 1% and 30% sage water
between 0.1% and 3% perfume or perfumed composition
q.s. distilled water.

More preferably, according to the invention, the makeup fixing cosmetic composition according to the invention comprises
between 0.25% and 2% styrene/acrylates copolymer
between 0.012% and 0.09% Biosaccharide Gum-4
between 1% and 10% rice powder
between 0.05% and 0.5% *Buddleja officinalis* flower extract
between 1% and 30% rose water
between 1% and 30% cornflower water
between 1% and 30% hamamelis water
between 1% and 30% sage water between 0.1% and 3% perfume or perfumed composition
q.s. distilled water.

Even more preferably, according to the invention, the makeup fixing cosmetic composition according to the invention comprises between 0.25% and 0.5% styrene/acrylates copolymer
between 0.06% and 0.09% Biosaccharide Gum-4
between 1% and 10% rice powder
between 0.05% and 0.5% *Buddleja officinalis* flower extract
between 1% and 30% rose water
between 1% and 30% cornflower water
between 1% and 30% hamamelis water
between 1% and 30% sage water
between 0.1% and 3% perfume or perfumed composition
q.s. distilled water.

Advantageously, the makeup fixing cosmetic composition according to the invention does not comprise any or comprises only a negligible amount (less than 1%) of emulsifier, which would wash off said fixing composition in the presence of perspiration, reducing the drying speed of said composition and thus reducing its hold. Furthermore, emulsifiers are ingredients that traditionally irritate the skin and are thus contrary to the technical problem that the applicant intends to solve by way of the present invention.

According to a preferred embodiment of the invention, the makeup fixing cosmetic composition according to the invention is in liquid form and can be pumped and then sprayed onto the skin, on top of the makeup, in the form of micro-droplets, allowing for uniform distribution of said composition.

According to another embodiment of the invention, the makeup fixing cosmetic composition according to the invention is in gel or emulsion form or in the form of a powder, preferably a pressed powder, and can be applied to the skin, on top of the makeup, using a finger or a special applicator.

According to another embodiment of the invention, the makeup fixing cosmetic composition according to the invention is directly incorporated in the makeup composition during the manufacture thereof, and intrinsically provides said makeup composition with a more lasting hold.

Another object of the present invention is the use of the makeup fixing cosmetic composition as described above and comprising the association of styrene/acrylates copolymer and Biosaccharide Gum-4, as a makeup fixing cosmetic composition.

A further object of the invention relates to a method for improving the hold of makeup compositions on the skin of a user, said method comprising the following steps:

1. applying one or more makeup products to the skin of the user; then
2. applying the makeup fixing cosmetic composition according to the invention to the skin of the user that is thus made up.

The makeup fixing cosmetic composition is preferably in liquid form and is applied to the user's skin in step 2 by means of spraying, preferably spraying micro-droplets. The micro-droplets advantageously have a diameter of at most 60 microns, having a dispersion of between approximately 30 microns and 150 microns. In order to achieve a result on the skin that is as homogenous as possible, the micro-droplets preferably have a diameter of at most 40 microns, having a dispersion of between approximately 30 microns and 60 microns.

This spraying can be achieved using a spray device such as a pump dispenser associated with a spray device or an aerosol.

Particularly preferably, the makeup fixing cosmetic composition is applied in step 2 in the form of an aerosol mist.

EXAMPLE

Figure 3:
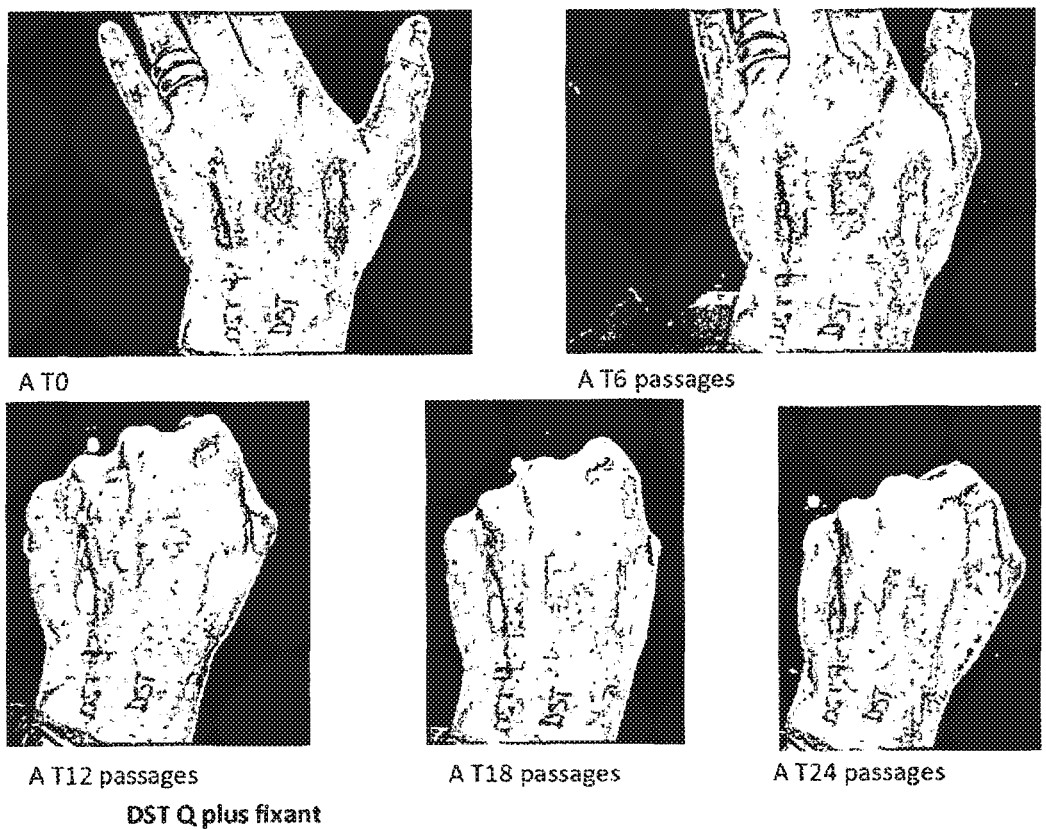
FIG. 3: Results of the example: is photographs of a hand made up with 3 lines of dark eye shadow, on top of which the association of styrene/acrylates copolymer and Biosaccharide Gum-4 according to the invention (on the hand to the left), only styrene/acrylates copolymer (on the hand in the center), and only Biosaccharide Gum-4 (on the hand to the right) have been applied, the hand being photographed at T0, then T after 6 passes, T after 12 passes, T after 18 passes, and T after 24 passes.

Evaluation and comparison of the makeup fixing action over time for 3 cosmetic formulations:
   DSTQ (styrene/acrylates copolymer and Biosaccharide Gum-4 according to the invention)
   DST (styrene/acrylates copolymer only)
   P (Biosaccharide Gum-4 only)
   Test Element
   Designation: DST Q, DST and P
   Container: glass spray bottles
   Form: aqueous liquids
   Storage condition: ambient temperature
   Site of application: back of the hand
   Conditions of use
   The bottle DST Q contains an association of styrene/acrylates copolymer (0.5%) and Biosaccharide Gum-4 (0.084%) in water
   The bottle DST contains a quantity of styrene/acrylates copolymer (0.5%) in water
   The bottle P contains a quantity of Biosaccharide Gum-4 (0.084%) in water
   Principle of the Study
   The principle of the test is based on determining the makeup fixing power of 3 cosmetic compositions, after successive rubbing.
   The aim is that of demonstrating that the association of styrene/acrylates copolymer and Biosaccharide Gum-4 has an action synergy having a makeup fixing power that is 2 to 8 times greater, over time, than if the styrene/acrylates copolymer or the Biosaccharide Gum had been used alone.
   The results were taken at T0, T+6 passes, T+12 passes, T+18 passes and T+24 passes; supported by photographs (FIG. 3).
   Course of the Study
   Material Used:
   Makeup: dark eye shadow by the cosmetic trademark MAC
   3 formulations to test (DSTQ, DST, P), each contained in a glass spray bottle Makeup remover pads: pad changed every 6 passes and between one formulation and another Test Protocol:

3 lines of dark eye shadow, of equal amounts, are painted onto the back of the same hand.

Figure 1:
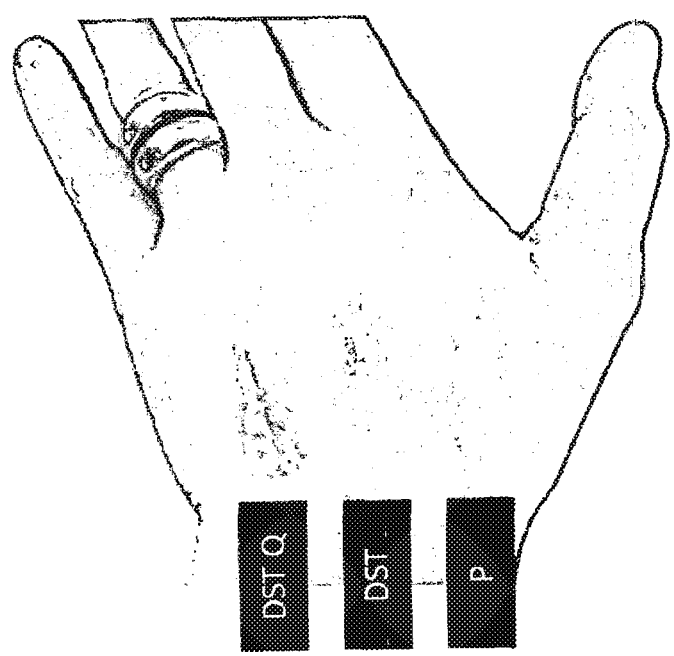
FIG. 1: is a photograph of a hand made up with 3 lines of dark eye shadow, on top of which the association of styrene/acrylates copolymer and Biosaccharide Gum-4 according to the invention (on the hand to the left), only styrene/acrylates copolymer (on the hand in the center), and only Biosaccharide Gum-4 (on the hand to the right) have been applied.

One spray selected from one of the 3 formulations DST Q, DST and P is vaporized onto each makeup line (FIG. 1).

Figure 2:
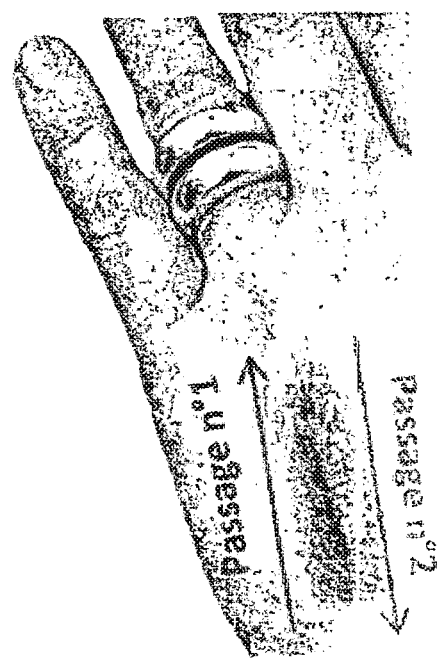
FIG. 2: is a photograph of a hand made up with one line of dark eye shadow and 2 opposing arrows, showing that the pad is applied in one direction and then in the other during passes in accordance with the protocol of the example.

Using a clean pad, each of the 3 made up regions is rubbed in turn. The pressure applied to the pad is substantially the same during each pass, made in one direction and then in the other (FIG. 2). Every 6 passes, the results are recorded, the photograph taken, and the pad changed.

6 passes on formulation DST Q
pad changed
6 passes on formulation DST
pad changed
6 passes on formulation P
pad changed
⟶ Evaluation of the results at T+6 passes
⟶ Photographs taken at T+6 passes
6 passes on formulation DST Q
pad changed
6 passes on formulation DST
pad changed
6 passes on formulation P
pad changed
⟶ Evaluation of the results at T+12 passes
⟶ Photographs taken at T+12 passes
6 passes on formulation DST Q
pad changed
6 passes on formulation DST
pad changed
6 passes on formulation P
pad changed
⟶ Evaluation of the results at T+18 passes
⟶ Photographs taken at T+18 passes
6 passes on formulation DST Q
pad changed
6 passes on formulation DST
pad changed
6 passes on formulation P
pad changed
⟶ Evaluation of the results at T+24 passes
⟶ Photographs taken at T+24 passes Results:

The results of the photographs are shown in FIG. 3. The intensity of the color remaining on the back of the hand was noted, on a scale of 1 to 10, following every 6 passes of the pad. The intensity of the remaining color makes it possible to demonstrate the makeup fixing power of each of the formulations, over time.

10 corresponds to the maximum color intensity, and thus to the highest fixing power, and 0 to a lack of remaining color, and thus a fixing power that is time-limited.

| Sample tested | T0 | T + 6 passes | T + 12 passes | T + 18 passes | T + 24 passes |
|---|---|---|---|---|---|
| DST Q styrene/acrylates copolymer + Biosaccharide Gum-4 + aqua (water) | 10 | 10 | 8 | 8 | 8 |
| DST styrene/acrylates copolymer + aqua (water) | 10 | 7 | 6 | 4 | 1 |
| P Biosaccharide Gum-4 + aqua (water) | 10 | 7 | 5 | 3 | 1 |

CONCLUSIONS

In view of the results, the formulation DST Q is the most fixing formulation and achieved a result of 8/10 after 24 passages, thus demonstrating the strength of the fixing power thereof: 8 times greater than the formulation DST or P;

The association of styrene/acrylates copolymer+Biosaccharide Gum-4 has a true action synergy that is far greater than if styrene/acrylates copolymer or Biosaccharide Gum-4 had been used alone.

The invention claimed is:

1. A makeup fixing cosmetic composition comprising: an association of styrene/acrylates copolymer and Biosaccharide Gum-4;
   between 0.25% and 20% styrene/acrylates copolymer;
   between 0.012% and 0.36% Biosaccharide Gum-4;
   between 1% and 10% rice powder;
   between 0.05% and 0.5% *Buddleja officinalis* flower extract;
   between 1% and 30% rose water;
   between 1% and 30% cornflower water;
   between 1% and 30% hammamelis water;
   between 1% and 30% sage water;
   between 0.1% and 3% perfume or perfumed composition; and
   qs distilled water.

2. The composition according to claim 1, characterized in that it is an aqueous solution in liquid form.

\* \* \* \* \*